(12) United States Patent
Shimizu

(10) Patent No.: US 6,440,167 B2
(45) Date of Patent: Aug. 27, 2002

(54) COLLAGEN MATERIAL AND ITS PRODUCTION PROCESS

(75) Inventor: Yasuhiko Shimizu, 39-676, Kohataogurayama, Uji-shi, Kyoto, 611-0002 (JP)

(73) Assignees: Yasuhiko Shimizu, Kyoto; Tapic International Co., Ltd., Tokyo, both of (JP)

( * ) Notice: Subject to any disclaimer, the term of this patent is extended or adjusted under 35 U.S.C. 154(b) by 0 days.

(21) Appl. No.: 09/761,593

(22) Filed: Jan. 16, 2001

Related U.S. Application Data

(62) Division of application No. 09/308,557, filed on May 20, 1999, now Pat. No. 6,277,397.

(30) Foreign Application Priority Data

| Nov. 20, 1996 | (JP) | ............................................. | 8-308856 |
| Nov. 20, 1996 | (JP) | ............................................. | 8-308857 |
| Sep. 29, 1997 | (JP) | ............................................. | 9-263374 |

(51) Int. Cl.⁷ .......................... A61F 5/00; A61F 13/00; A61F 15/00; A61F 2/10
(52) U.S. Cl. ............................... 623/15; 602/3; 602/41; 602/42; 602/43; 602/44; 602/45; 602/48; 602/60
(58) Field of Search ................................ 523/15, 66, 1; 602/3, 41, 42, 43, 44, 45, 48, 60

(56) References Cited

U.S. PATENT DOCUMENTS

| 4,578,067 A | * | 3/1986 | Cruz, Jr. ....................... 602/50 |
| 5,350,583 A | * | 9/1994 | Yoshizato et al. ........... 424/484 |

\* cited by examiner

*Primary Examiner*—Nathan M. Nutter
(74) *Attorney, Agent, or Firm*—David G. Conlin; Robert L. Buchanan; Edwards & Angell, LLP

(57) ABSTRACT

The present invention relates to a collagen material comprising a laminate in which a collagen ultra-fine fibrous non-woven fabric-like multi-layer structure is sandwiched between non-fibrous collagen layers, a thread-like material containing said collagen material, their production processes, and a medical material containing said collagen material, and particularly a medical alternative membrane comprised of said medical material. These use collagen for their raw material without combining the use of a synthetic polymer material, possess physical properties to an extent that allows suturing while still maintaining the biochemical properties inherently possessed by collagen, and the alternative medical membrane can be used as a material for filling in the missing portions of biomembranes such as endocranium, pericardium, pleura, peritonium or serous membrane, presents no ethical problems, is in stable supply, has no risk of infection, does not cause cell degeneration, allows control of the rate of degradation following application to the body, and has an action that promotes regeneration of biomembranes.

3 Claims, 5 Drawing Sheets

COLLAGEN MATERIAL AND ITS
PRODUCTION PROCESS

This application is a division of application Ser. No. 09/308,557, filed May 20, 1999, now U.S. Pat. No. 6,277,397, which is a 371 of PCT/JP97/0420, filed Nov. 19, 1997.

TECHNICAL FIELD

The present invention relates to a collagen material comprising a laminate in which a collagen ultra-fine fibrous non-woven fabric-like multi-layer structure is sandwiched between non-fibrous collagen layers, a thread-like material containing said collagen material, and their production processes, as well as a medical material containing said collagen material, and particularly a medical alternative membrane comprised of said medical material.

BACKGROUND ART

Among the various materials used as medical materials, animal collagen has excellent bioaffinity and histocompatibility, low antigenicity, has the action of promoting host cell differentiation and growth, has a hemostatic action, and is completely broken down and absorbed in the body. Consequently, it has properties that are particularly suitable for use as a medical material. At present, animal collagen types I through XIX have been discovered, collagen types I through V are used in a variety of ways as medical materials. In particular, type I collagen, which is useful as an extracellular matrix, is used most commonly. These collagens are extracted and purified from the connective tissue of various organs such as skin, bone, cartilage, tendon, and viscus of animals such as cows, pigs, birds, kangaroos and so forth by acidic solubilization, alkaline solubilization, neutral solubilization and enzymatic solubilization. Extracted collagen used conventionally is one that has been broken down to monomers and oligomers at the molecular level, and is stored in the form of a powder or liquid. Since these extracted collagens are in a state in which collagen molecules are broken down to monomers and oligomers, when they come in contact with water, body fluids or blood, they form a sol extremely rapidly. Consequently, when using these collagens by molding as medical materials, they are either used by covering the surface of a synthetic polymer material such as Nylon or silicone with collagen to give the material a certain degree of strength during processing, or are used by subjecting the molded product of the extracted collagen to chemical crosslinking treatment using a crosslinking agent or to physical crosslinking treatment using radiation, electric beam, ultraviolet rays or heat in order to hold the shape of the material for a certain period of time in the case of applying to the body. In addition, although these extracted collagens may be used as thread for medical treatment by forming into the shape of a thread, wet spinning is used for its spinning.

However, in the case of a material in which collagen is combined with a synthetic polymer material, the synthetic polymer material remains in the body as a foreign object resulting in susceptibility to the occurrence of disorders such as granulation and inflammation, and this type of material cannot be applied to all cells and viscera. In addition, even if crosslinking treatment is performed on collagen materials, since there is hardly increase at all in the physical properties of the collagen material, and particularly tear strength, it was not possible to process this material for use as a medical material requiring suturing. In addition, when a crosslinking agent such as glutaraldehyde or epoxy is used, not only does the toxicity of the crosslinking agent on the body become a problem, but there is also the disadvantage of the biochemical properties inherently possessed by collagen, and particularly promotional effects on cell growth, being lost. In addition, in the case of physical crosslinking treatment, the crosslinking rate is unstable and it is unable to give adequate physical properties to the collagen material. In addition, it has also been difficult to perform crosslinking treatment so that the absorption rate in the body can be controlled. On the other hand, since spun collagen does not have sufficient strength, it is not adequate for use as suture.

On the other hand, although it is necessary to close by resuturing an opened endocranium, pericardium, pleura, peritoneum or serous membrane when closing a surgical wound after performing surgery on the brain or various viscera for the treatment of various diseases or trauma, there are many cases in which a missing portion forms in the membrane that prevents a surgical wound from being completely closed due to the formation of a shortened portion depending on the length of the suture or the membrane being partially severed. If such a missing portion is left uncorrected, the viscera such as the brain, heart, lung, and intestine may herniate from the area where the membrane is missing resulting in a serious disorder, or water or air may escape from the viscera or area around the viscera preventing the surgical wound from healing. In addition, since the viscera may adhere to surrounding tissues, the tissue may be damaged thereby preventing the obtaining of a favorable prognosis. Consequently, freeze-dried human endocranium removed from cadavers or porous elastic polytetrafluoroethylene film (EPTFE) (Tissue Goretex, trade name), polypropylene mesh, Teflon sheet or Dacron sheet and so forth are used as alternative medical membranes that can be used as fillers for these missing portions. In addition, a copolymer of lactic acid and ε-caprolactone (50:50) is currently being developed. In addition, methods involving the use of the patient's own fascia lata or the patient's own pericardium, skin or muscle and so forth are also performed as a last resort.

However, with respect to the use of human endocranium, adhesion occurs between the filled human endocranium and brain parenchymal tissue. Not only does this have the risk of causing epileptic attacks following surgery, there is also the ethical problem of obtaining specimens from human cadavers as well as the problem of the supply being extremely limited. More recently, the occurrence of Creutzfeldt-Jakob Disease (CJD) caused by transplanted endocranium has been reported in patients receiving endocranial transplants (J. Neurosurgery, 21(2): 167-170, 1993). In Japan, human endocranium is currently not used. In addition, since EPTFE materials and so forth are not broken down in the body but rather remain as foreign objects, they easily cause infection or, when in contact with body tissue, end up causing fatty degeneration of tissue cells and so forth, and are known to frequently cause post-operative complications. Copolymers of lactic acid and ε-caprolactone are degradable in the body. Although they gradually are broken down after being applied to the body, a long period of time on the order of nearly two years is required for them to be completely broken down and absorbed. Consequently, they also remain in the body for a short time as foreign objects, cause inflammation in tissue during the degradation process and form granuloma. Since this copolymer uses the (L) form of lactic acid as its monomer, lactic acid may crystallize in the copolymer causing inflammation. Moreover, both EPTFE and copolymer of lactic acid and ε-caprolactone do not have the action of promoting regeneration of biomembranes. In addition, methods using the patient's own fascia lata and so forth place a significant burden on both the patient and physician.

Although materials such as the above-mentioned EPTFE, polypropylene mesh (Marlex), human dried endocranium and glutaraldehyde (GA)-treated bovine pericardium have been used in the past as pericardium fillers, EPTFE and human dried pericardium have the disadvantages described above. In addition, polypropylene mesh causes strong adhesion between itself and the heart. Since GA-treated bovine pericardium remains in the body without being absorbed or broken down, it causes deterioration due to mineral deposition, and complications due to interstitial pneumonia caused by an immune reaction to the bovine pericardium have also been observed.

In addition, although polyglycolic acid non-woven fabric and bovine pericardium have been used as a pleural filler or for an auto-suture to reduce the escape of air from the surgical site following lung surgery, polyglycolic acid causes strong adhesion and because it is not transparent, it is difficult to be used for an auto-suture. In addition, bovine pericardium has the disadvantages previously described.

For these reasons, a need has arisen for the development of a collagen material that uses collagen for its raw material without combining the use of a synthetic polymer material, possesses physical properties to an extent that allows suturing while still maintaining the biochemical properties inherently possessed by collagen, and retains its shape for a certain amount of time even after application to the body; its production process; and, a medical material on which it is based, examples of which include a peripheral neural tube, artificial spine, artificial esophagus, artificial trachea, artificial blood vessel, artificial valve or artificial alternative medical membranes such as artificial endocranium, artificial ligaments, artificial tendons, surgical sutures, surgical fillers, surgical reinforcement, wound protecting materials, artificial skin and artificial cornea. In particular, there has arisen a strong need in the clinical setting for the development of various types of medical materials that can be used as alternative medical membranes which present no ethical problems, are in stable supply, prevent adhesion of the surgical wound following surgery after being applied to the body, have no risk of infection, do not cause tissue degeneration, allow control of the rate of degradation following application, and have an action that promotes regeneration of biomembranes, especially endocranium, pericardium, pleura, peritoneum or serous membrane.

DISCLOSURE OF THE INVENTION

As a result of earnest research in order to solve the above-mentioned problems, the inventors of the present invention found that a collagen material comprising a laminate in which a collagen ultra-fine fibrous non-woven fabric-like multi-layer structure is sandwiched between non-fibrous collagen layers has excellent properties as a medical material as well as physical properties that allow suturing, thereby leading to completion of the present invention. Namely, the present invention relates to a collagen material comprising a laminate in which a collagen ultra-fine fibrous non-woven fabric-like multi-layer structure is sandwiched between non-fibrous collagen layers. In addition, the present invention relates to a production process of the above-mentioned collagen material comprising freezing a collagen solution layer; freeze-drying to form a fine fibrous collagen layer; compressing; repeating a process consisting of immersing in a collagen solution and air-drying; followed by subjecting to crosslinking treatment. Moreover, the present invention relates to a thread-like material containing a collagen material comprising a laminate in which a collagen ultra-fine fibrous non-woven fabric-like multi-layer structure is sandwiched between non-fibrous collagen layers; and, a production process of the above-mentioned thread-like material comprising wet-spinning a collagen solution to obtain collagen threads; freezing the collagen threads; freeze-drying; compressing the collagen threads; repeating a process consisting of immersing in collagen solution and air-drying; followed by subjecting to crosslinking treatment. Moreover, the present invention relates to a medical material containing a collagen material comprising a laminate in which a collagen ultra-fine fibrous non-woven fabric-like multi-layer structure is sandwiched between non-fibrous collagen layers, an alternative medical membrane comprised of said medical material, and particularly an alternative medical membrane having a crosslinked gelatin gel layer or hyaluronic acid layer on one or both sides.

BEST MODE FOR CARRYING OUT THE INVENTION

Figure 1:
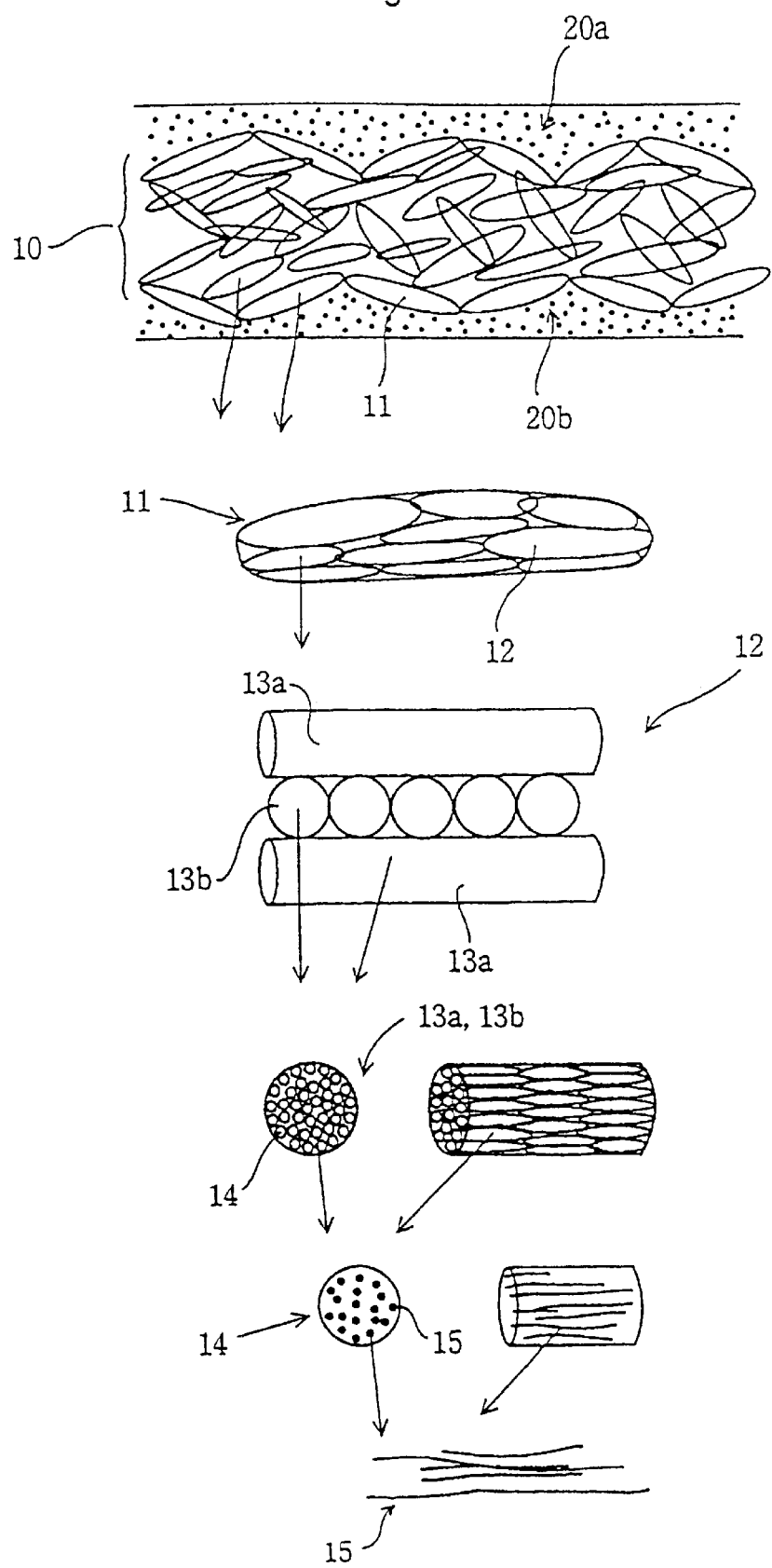
FIG. 1 shows the structure of the collagen material of the present invention.
Figure 2:
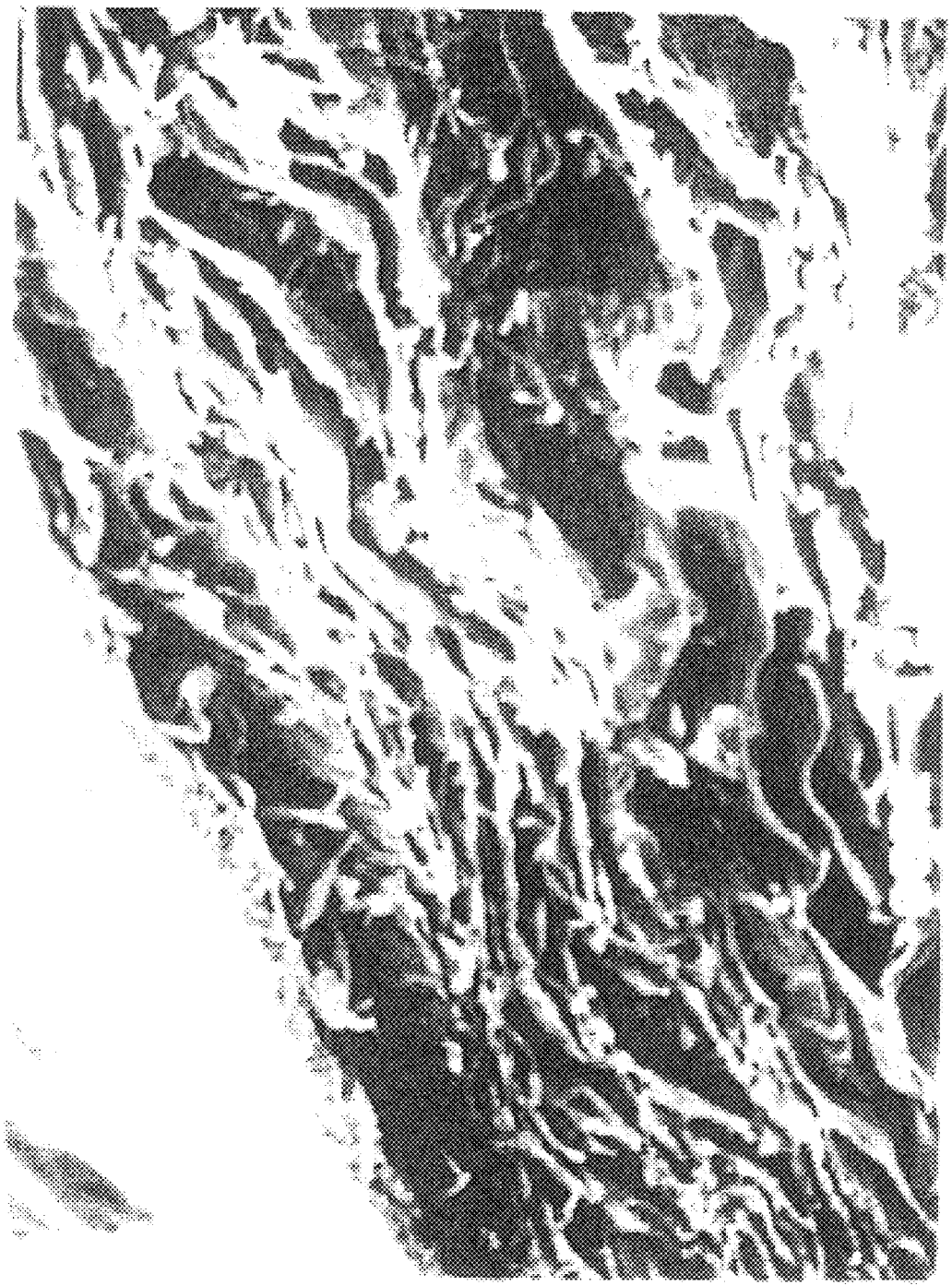
FIGS. 2 through 5 are electron micrographs showing the form of each fiber of the collagen material of the present invention.
Figure 3:
Figure 4:
Figure 5:

FIG. 1 illustrates the structure of the collagen material of the present invention. In this collagen material, ultra-fine fibers 15, composed of several collagen molecules and having a diameter of about 5 nm, serve as the basic unit to form fine fibers 14 having a diameter of about 50 nm, and these form narrow fibers 13a and 13b having a diameter of about 2 $\mu$m. As shown in the drawing, these narrow fibers 13a and 13b form fibers 12 having a diameter of about 6 $\mu$m by alternately overlapping as warp and weft, and these overlap in the coaxial direction to form plate fibers 11 having a diameter of about 20–50 $\mu$m. These plate fibers 11 form collagen ultra-fine fibrous non-woven fabric-like multi-layer structure 10, and non-fibrous collagen layers 20a and 20b in which collagen molecules are dispersed in the form of monomers and oligomers are present on its outside. Moreover, collagen molecules are also incorporated between the plate fibers of the non-woven fabric-like multi-layer structure. FIG. 2 is an electron micrograph of a cross-section of the collagen material of the present invention. FIG. 3 indicates a fiber 12 formed by alternate overlapping of narrow fibers 13a and 13b. FIG. 4 indicates ultra-fine fibers 15 and fine fiber 14 which is formed by using ultra-fine fibers 15 as the basic unit. FIG. 5 indicates ultra-fine fiber 15.

Examples of collagen that can be used as the raw material of the collagen material comprised of a laminate in which a collagen ultra-fine fibrous non-woven multi-layered structure is sandwiched between non-fibrous collagen layers include various types of collagen used in the prior art, and preferably neutral solubilized collagen, acidic solubilized collagen, alkaline solubilized collagen or enzymatic solubilized collagen. Among these, enzymatic solubilized collagen is particularly preferable since it involves treatment of insoluble collagen with enzyme (e.g., pepsin, trypsin, chymotrypsin, papain and pronase), causing the strongly antigenic telopeptide portion in the collagen molecules to be removed by this treatment resulting in decreased antigenicity. There are no particular restrictions on the origin of this collagen, and in general, type I collagen or mixed type I and type III collagen can be used which is obtained by extraction and purification from the skin, bone, cartilage, tendon, viscera and so forth of animals such as cows, pigs, rabbits, sheep, kangaroos, birds and fish, etc.

When the collagen material of the present invention having an ultra-fine fiber structure as described above is compared with a material comprised only of non-fibrous collagen having an amorphous structure in which collagen molecules are dispersed in the state of monomers and oligomers that have been used in the past as various types of medical materials, although the former retains the action on the body inherently possessed by collagen, in comparison with the latter, not only does it have excellent physical properties, and particularly excellent tear strength, but the rate of absorption in the body is also adequately extended. In addition, a thread-like material containing the collagen material of the present invention is in the form of a thread of a collagen material comprising a laminate in which a collagen ultra-fine fibrous non-woven fabric-like multi-layer structure is sandwiched between non-fibrous collagen layers. In addition, a medical material containing the collagen material of the present invention is a processed product of a collagen material comprising a laminate in which a collagen ultra-fine fibrous non-woven fabric-like multi-layer structure is sandwiched between non-fibrous collagen layers, into various types of medical materials. Examples of forms of medical materials include membranes, tubes, pouches and clumps. One particular example of an application of this medical material is an alternative medical membrane, and more specifically, a preferable example is an alternative medical membrane having a crosslinked gelatin gel layer or hyaluronic acid layer on one or both of its sides. In this case, the thickness is preferably about 0.1–5 mm.

The gelatin gel layer that is able to be present on the surface of the alternative medical membrane of the present invention acts as an adhesion preventive layer for preventing extension of cells from the surrounding body tissue at locations requiring prevention of adhesion due to the action of gelatin that impairs cell adhesion and growth. In addition, hyaluronic acid has the effect of improving collagen stability as well as the effect of preventing adhesion. In the alternative medical membrane of the present invention, since it is necessary for the gelatin gel layer or hyaluronic acid layer to remain without being degraded or absorbed for about 3–4 weeks after applying to the body, this gelatin gel layer or hyaluronic acid layer is crosslink treated.

In order to prepare the collagen material of the present invention comprising a laminate in which a collagen ultra-fine fibrous non-woven fabric-like multi-layer structure is sandwiched between non-fibrous collagen layers, an approximately 1N hydrochloric acid solution (pH of about 3) of collagen is prepared after extraction and purification as described above (the collagen concentration is preferably about 0.5–3 wt %, and particularly preferably about 1 wt %), and a collagen hydrochloric acid solution layer is formed in a container such as a Petri dish so that the liquid layer has an arbitrary uniform thickness using any routine method such as pouring. Although the thickness of the collagen hydrochloric acid solution layer is determined according to the application of the collagen material of the present invention, in the case of using, for example, as an alternative medical membrane in the form of an endocranium, the thickness is preferably about 1–5 cm, and particularly preferably about 1–3 cm. This is then frozen preferably at about −10 to −196° C., and particularly preferably at about −20° C., for at least about 6 hours, preferably about 6–48 hours, and particularly preferably about 24 hours. As a result of freezing, fine pieces of ice are formed between the collagen molecules dispersed in the hydrochloric acid solution, and layer separation occurs in the collagen hydrochloric acid solution resulting in the formation of fine fibers due to rearrangement of the collagen molecules. If the freezing time is less than 6 hours, since the collagen hydrochloric acid solution is not adequately frozen, there is insufficient formation of fine fibers of the collagen molecules, thereby preventing the obtaining of adequate physical properties. Next, the above-mentioned frozen collagen hydrochloric acid solution is freeze-dried in a vacuum preferably at about −40 to −80° C., and particularly preferably at about −80° C., preferably for about 24–48 hours, and particularly preferably for about 48 hours. As a result of freeze-drying, together with the fine pieces of ice between the collagen molecules being vaporized, the ultra-fine fibers comprised of collage molecules serve as the basic units to obtain a non-woven fabric-like collagen layer composed by fine fibers, narrow fibers, fibers and plate fibers as previously described.

Next, the non-woven fabric-like collagen layer obtained in the manner described above is compressed to a uniform thickness using a press apparatus. As a result of compressing, the residual time of the collagen material of the present invention in the body is controlled. For example, in the case of using a 1 wt % collagen hydrochloric acid solution, compression is performed for 15 seconds at a pressure of, for example, 200 kg/cm² over a compression ratio range of 30–60. Next, the compressed collagen layer is immersed in a collagen hydrochloric acid solution and air-dried. This immersion and air-drying step is repeated 5–20 times. The collagen hydrochloric acid solution used here is a non-fibrous collagen solution containing about 0.5–3 wt %, and particularly about 2 wt %, of extracted and purified collagen in about 1N hydrochloric acid in which collagen molecules are dispersed in the state of monomers and oligomers, and as a result of immersing the compressed collagen layer in this collagen solution, the collagen molecules dispersed in the collagen solution are incorporated between the plate fibers of the non-woven fabric-like collagen layer. As a result, anchoring effects are demonstrated which, together with providing strength, increase stability to water. Although it is suitable to repeat this immersion and air-drying step 5–20 times, the number of repetitions can be suitably determined within this range according to the application of the collagen material of the present invention. Next, the immersed and air-dried collagen layer is subjected to crosslinking treatment to obtain the collagen material of the present invention comprising a laminate in which a collagen ultra-fine fibrous non-woven fabric-like multi-layer structure is sandwiched between non-fibrous collagen layers. As a result of performing crosslinking treatment, a medical material containing the collagen material of the present invention can be adjusted so as to remain for a desired period of time after its application to the body. It is preferable to perform thermal dehydration crosslinking to facilitate control of the degree of crosslinking and to eliminate the effect of the crosslinking agent on the body. In order to perform thermal dehydration crosslinking, the immersed and air-dried collagen layer obtained above is heated in a vacuum preferably at about 105–150° C., and particularly preferably at about 140° C., preferably for about 6–48 hours, and particularly preferably for about 24 hours. If heated at a temperature below 105° C., a sufficient crosslinking reaction does not take place. If heated at a temperature above 150° C., the collagen ends up denaturing. Next, the collagen material of the present invention obtained in the above-mentioned process may be sterilized as necessary by ethylene oxide gas treatment, ultraviolet irradiation or gamma ray irradiation. The collagen material of the present invention produced in the manner described above has, in the dry state, single-point support tension of at least about 23N and particularly 45N or more, rupture resistance tension of at least about 170N and particularly 230N or more, and in the wet state, single-point support tension of at least 2N and particularly 6N or more, and rupture resistance tension of at least 12N and particularly 23N or more (in the case of a collagen material having a specific gravity of 0.74 g/cm$^3$ and thickness of 1 mm). Since this collagen material has superior strength to collagen materials of the prior art, it can be processed into various types of medical materials and can also be sutured. In addition, it is able to retain its shape for about 3–8 weeks in the case of being applied in the body. Moreover, it also retains the inherent properties of collagen as a medical material.

Since the collagen material of the present invention has excellent strength, it can also be used as surgical suture. A thread-like material containing the collagen material of the present invention can be prepared in the manner described below. An about 1N hydrochloric acid solution (pH of about 3) of extracted and purified collagen is prepared (the collagen concentration is preferably about 0.5–3 wt %, and particularly preferably about 1 wt %), and this is sprayed into a coagulation bath from a nozzle having an aperture of preferably about 50–300 µm, and particularly preferably about 100 µm, to perform wet spinning. The resulting collagen thread is frozen and freeze-dried under the same conditions as described above to form a collagen thread. Next, this collagen thread is compressed under the same conditions as described above. Next, the compressed collagen thread is immersed in a collagen hydrochloric acid solution (about 2 wt % in about 1N hydrochloric acid) and air-dried. This step is repeated 5–20 times. Next, the immersed and air-dried collagen thread is subjected to crosslinking treatment under the same conditions as described above to obtain a thread-like material containing the collagen material of the present invention.

In the case of processing the collagen material of the present invention prepared in the manner described above into an alternative medical membrane having a crosslinked gelatin gel layer or hyaluronic acid layer on one or both of its sides, in the case of a gelatin gel layer, the gelatin gel layer is formed by using an aqueous gelatin solution of preferably about 2–70 wt % and particularly preferably about 60 wt %. However, in the case of using an aqueous gelatin solution of about 60 wt %, the gelatin gel layer is formed to a thickness of preferably about 0.1–5 mm and particularly preferably about 1 mm when wet, or preferably about 0.06–3 mm and particularly preferably about 0.6 mm when dry. Although the gelatin gel layer may be formed by a method such as coating or immersion, for example, the aqueous gelatin solution may be poured into a container such as a Petri dish to the required thickness, and the collagen material of the present invention obtained in the manner described above may be placed on top of it and allowed to stand to allow the gelatin to gelatinize. In the case of forming a gelatin gel layer on both sides, a similar process is performed on the other side as well to form gelatin gel layers on both sides.

Next, the collagen material on which a gelatin gel layer has been formed on one or both sides obtained in this manner is subjected to a second crosslinking treatment. As a result of performing this crosslinking treatment, the rate of degradation and absorption of the gelatin gel layer is controlled. Thermal dehydration crosslinking is preferable for the crosslinking method for the same reasons as described above. In order to allow the gelatin gel layer to remain for about 3–4 weeks after application to the body, the collagen material on which the above-mentioned gelatin gel layer has been formed is subjected to thermal dehydration crosslinking treatment in a vacuum preferably at about 105–150° C. and particularly preferably about 140° C. for preferably about 6–48 hours and particularly preferably about 24 hours. If the temperature is below about 105° C., the crosslinking reaction does not occur adequately, and if the temperature exceeds 150° C., the collagen ends up denaturing.

The crosslinked gelatin gel layer formed in this manner has the role of preventing the collagen portion of the present alternative medical membrane from adhering to surrounding tissue until each biomembrane is regenerated, and the gelatin gel layer remains without being degraded or absorbed for about 3–4 weeks until biomembrane extends and regenerates from around the membrane missing portion and fills in the missing portion of the membrane.

In the case of forming a hyaluronic acid layer, an aqueous sodium hyaluronate solution layer is formed by a method such as coating or immersion on one or both sides of the collagen material of the present invention obtained in the manner described above by using an aqueous sodium hyaluronate solution of preferably about 0.5–2.0 mg/ml and particularly preferably about 1.0 mg/ml, after which this aqueous solution layer is air-dried to form a hyaluronic acid layer. The aqueous sodium hyaluronate solution layer is formed to a thickness of preferably about 0.5–4.0 mm and particularly preferably about 2 mm in the wet state, or preferably about 0.1–2.0 mm and particularly preferably about 1.0 mm in the dry state (in the case of an aqueous solution of about 1.0 mg/ml) so that the hyaluronic acid layer is able to remain without being degraded or absorbed for about 3–4 weeks until the biomembrane extends and is regenerated from around the missing portion of the membrane to be repaired and fills in the missing portion of the membrane. In order to fix the hyaluronic acid on the surface of the collagen material and form the hyaluronic acid layer, a second crosslinking treatment is performed. However, in the case of hyaluronic acid, it is preferable to perform crosslinking treatment with water-soluble carbodiimide (WSC). In this case, it is preferable to premix WSC with aqueous sodium hyaluronate solution and apply to the collagen material with sodium hyaluronate to crosslink the carboxyl groups of the collagen with the amino groups of the hyaluronic acid. The concentration of WSC contained in aqueous sodium hyaluronate solution is preferably about 5–20 mg/ml and particularly preferably about 8–15 mg/ml. An aqueous solution containing this sodium hyaluronate and WSC is prepared, it is stirred well and coated onto one or both sides of a collagen material preferably to a thickness of about 1 mm followed by air-drying to form the hyaluronic acid layer.

The collagen material of the present invention prepared in the manner described above has superior physical properties and, particularly superior tear strength to extracted collagen materials of the prior art, and it can be processed into various medical materials using the collagen material alone without laminating to synthetic polymer materials and so forth, and can also be used for suturing. In addition, in the case of applying the collagen material of the present invention in the body, it is able to retain its shape for about 3–8 weeks without immediately dissolving. For these reasons, by processing the collagen material of the present invention into the form of a membrane, tube, pouch or clump according to the particular application, it can be used as various types of medical materials. For example, it can be used as a peripheral neural tube, artificial spinal cord, artificial esophagus, artificial trachea, artificial blood vessel, artificial valve, artificial alternative medical membrane such as alternative endocranium, an artificial ligament, artificial tendon, surgical suture, surgical filler, surgical reinforcement, wound protecting material, artificial skin and artificial cornea, and can accelerate recovery and regeneration of injured body tissue. Alternatively, it can also be used as a pressure styptic or three-dimensional medium in cell culturing.

In addition, an alternative medical membrane comprising the medical material of the present invention obtained in the manner described above can be used to prevent adhesion of viscera and surrounding tissue in portions of missing membrane by filling in membrane missing portions following various types of surgery. In the alternative medical membrane of the present invention, an alternative medical membrane of the present invention is used in which a gelatin gel layer or hyaluronic acid layer is formed on one or both sides so that the crosslinked gelatin gel layer or hyaluronic acid layer is facing the side that comes in contact with surrounding tissue for which it is necessary to prevent adhesion. In the case of using the present alternative medical membrane as an alternative membrane of the pericardium, an alternative membrane is used in which a gelatin layer or hyaluronic acid layer is formed on both sides so that the gelatin gel or hyaluronic acid layer is facing the sides that come in contact with the surrounding tissue, while in the case of using the present alternative medical membrane as an alternative membrane of the pleura, peritoneum or serous membrane, an alternative membrane is used in which a gelatin gel layer or hyaluronic acid layer is formed on one side so that the gelatin gel or hyaluronic acid layer is facing the side that comes in contact with the surrounding tissue. In the case of using as an alternative membrane of the endocranium, an alternative membrane can be used in which a gelatin gel layer or hyaluronic acid layer is formed on either one or both sides. In the case of using an alternative membrane in which a gelatin gel layer or hyaluronic acid layer is formed on one side, the membrane is used so that the gelatin gel layer or hyaluronic acid layer is facing the side that comes in contact with brain parenchymal tissue. Moreover, this alternative membrane material can also be used as reinforcement for suturing blood vessels, digestive tract, trachea, ureter, urinary bladder, serous membrane or periodontal membrane.

The alternative medical membrane of the present invention that serves as a material for filling missing portions of biomembranes in the manner described above can be used as an alternative membrane of the endocranium, pericardium, pleura, peritoneum or serous membrane. When the present alternative membrane is applied to a surgical wound, while the biomembrane such as the endocranium, pericardium, pleura, peritonium or serous membrane that remains around the surgical wound extends and regenerates from the site in contact with the present alternative membrane by using the collagen portion of the present alternative membrane as a foothold for regeneration, adhesion is prevented at sites where body tissue comes in contact with the gelatin gel layer or hyaluronic acid layer to prevent cell invasion and extension so that ultimately, the missing portion is filled in by the regenerated biomembrane, after which the present alternative membrane is completely eliminated as a result of degradation and absorption by the body.

As described above, although the collagen material of the present invention as well as a medical material containing the collagen material of the present invention, and particularly an alternative medical membrane, have tear strength that is superior to conventional collagen materials and medical materials in which they are contained, when using the present medical material as, for example, an artificial urinary bladder, there are cases in which even greater strength is required. Consequently, the collagen material of the present invention and a medical material containing the collagen material of the present invention may have, when so required, a sheet-like mesh intermediate comprised of a biodegradable, absorbable material inside. Examples of biodegradable, absorbable materials include polyglycolic acid, polylactic acid, copolymer of glycolic acid and lactic acid, polydioxanone, copolymer of glycolic acid and trimethylene carbonate, or a mixture of polyglycolic acid and polylactic acid. Sheet-like mesh intermediates composed of these materials are in the form of a mesh sheet, woven fabric, non-woven fabric or sheet containing punched holes having a hole diameter of, for example, about 50–2000 μm. Although their thickness is, for example, about 100–2000 μm, the hole diameter and thickness of the mesh intermediate can be suitably changed according to the specific application.

In order to prepare a collagen material having a sheet-like mesh intermediate composed of a biodegradable, absorbable material inside, a sheet-like mesh intermediate like that described above is left immersed in a collagen hydrochloric acid solution when forming the collagen ultra-fine fibrous non-woven fabric-like multi-layer structure, after which the collagen hydrochloric acid solution layer is subjected to following steps such as freezing and freeze-drying.

The following provides an explanation of the present invention through its examples.

EXAMPLE 1

A 1N hydrochloric acid solution of 1 wt % collagen was prepared using pigskin collagen, the solution as poured into a Petri dish to prepare collagen solution layers having thicknesses of 6, 12 and 18 mm, respectively. The layers were then frozen for 24 hours at −20° C., and then freeze-dried for 24 hours at −80° C. Next, the layers were hot pressed for 15 seconds at room temperature and a pressure of 200 kg/cm$^2$ using a press to obtain layers having thicknesses of about 0.2, 0.3 and 0.5 mm, respectively. A 1N hydrochloric acid aqueous solution of 2 wt % collagen was prepared using the above-mentioned collagen for the raw material, and the pressed collagen layers obtained above were immersed in this collagen solution and air-dried. This immersion and air-drying step was repeated 5 or 10 times after which the immersed and air-dried layers were subjected to thermal crosslinking treatment in a vacuum at 140° C. for 24 hours to obtain collage materials of the present invention.

The single-point support tension and rupture resistance tension were measured in the wet and dry states for the collagen materials of the present invention prepared above according to the methods described below.

Short test pieces were prepared measuring 15×40 mm. Tension was applied uniformly at ISO speed B (5 mm/min) in the axial direction of the test pieces using a digital push-pull gauge (Aikoh Engineering CPU gauge) in a constant temperature, constant humidity bath at 25° C. and humidity of 50% according to the method described below, and the maximum tension at which the membrane ruptures was measured in both the dry and wet states (hydrated for 1 minute in physiological saline at 37° C. or hydrated for 24 hours in physiological saline at room temperature).

1. Single-Point Support Tension

A thread (4-0 proline or 2 dexon) was sutured and anchored at a site 5 mm to the inside from the center of the end of each test piece, while tension was applied to the other end by uniformly clamping with a clip.

2. Rupture Resistance Tension

Tension was applied to both ends of each test piece by uniformly clamping both ends with clips.

The results are shown in the table below.

| Thickness of collagen hydrochloric acid solution layer (before freezing) | Compression ratio | Dry state | | Wet state | |
|---|---|---|---|---|---|
| | | Single-point support tension | Rupture resistance tension | Single-point support tension | Rupture resistance tension |
| 6 mm | 0.03 | 6.3 | 51.4 | 0.74 | 4.89 |
| 12 mm | 0.02 | 16.7 | 78.3 | 2.05 | 8.92 |
| 18 mm | 0.03 | 27.8 | 110.2 | 4.93 | 9.47 |

| | Dry state | | Wet state | |
|---|---|---|---|---|
| | Single-point support tension | Rupture resistance tension | Single-point support tension | Rupture resistance tension |
| Immersion and air-drying repeated 5 times | 14.4 | 50.3 | 0.9 | 4.61 |
| Immersion and air-drying repeated 10 times | 27.8 | 110.2 | 4.93 | 9.47 |

(Units: N)

According to the above results, the collagen materials of the present invention were shown to have excellent properties that are able to withstand suturing.

Industrial Applicability

Since the collagen material of the present invention comprising a laminate in which a collagen ultra-fine fibrous non-woven fabric-like multi-layer structure is sandwiched between non-fibrous collagen layers has physical properties that allow suturing even though it retains biochemical properties inherently possessed by collagen, it can be widely used as various types of medical materials. In addition, the alternative medical membrane of the present invention presents no ethical problems, can be provided in stable supply, and can be sutured to a surgical wound as a material that fills in the missing portion of a biomembrane or as a material that prevents adhesion. In addition, while it demonstrates effects that prevent adhesion, since it remains for a period of time after suturing until the biomembrane regenerates and is then gradually degraded and absorbed, it does not cause inflammation and so forth as a result of remaining in body tissue for a long period of time, thereby allowing it to be used safely.

What is claimed is:

1. A medical material having a sheet-like mesh intermediate composed of a biodegradable, absorbable material inside a collagen ultra-fine fibrous non-woven fabric-like multi-layer structure, wherein the biodegradable, absorbable material is a polyglycolic acid, polylactic acid, copolymer of glycolic acid and lactic acid, polydioxanone, copolymer of glycolic acid and trimethylene carbonate; or a mixture of polyglycolic acid and polylactic acid.

2. An alternative medical membrane comprising the medical material as set forth in claim 1.

3. The alternative medical membrane of claim 2 having a crosslinked gelatin gel layer or hyaluronic acid layer on one or both sides.

* * * * *